US008617213B2

(12) United States Patent
Moore et al.

(10) Patent No.: US 8,617,213 B2
(45) Date of Patent: Dec. 31, 2013

(54) LOW PROFILE TRANSVERSE CONNECTOR (75) Inventors: Brandon Moore, Leesburg, VA (US);
Scott A. Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 1107 days.

(21) Appl. No.: 11/760,159

(22) Filed: Jun. 8, 2007

(65) Prior Publication Data

US 2008/0306538 A1  Dec. 11, 2008

(51) Int. Cl.
*A61B 17/70* (2006.01)

(52) U.S. Cl.
USPC ........................................................ 606/253

(58) Field of Classification Search
USPC ............... 606/246, 250–253, 279, 86 A, 266; 403/391, 396, 399
See application file for complete search history.

(56) References Cited

U.S. PATENT DOCUMENTS

| | | | | |
|---|---|---|---|---|
| 6,234,705 B1 * | 5/2001 | Troxell | ........................ | 403/237 |
| 6,306,137 B2 * | 10/2001 | Troxell | ........................ | 606/252 |
| 6,402,751 B1 * | 6/2002 | Hoeck et al. | .................. | 606/252 |
| 6,761,721 B2 * | 7/2004 | Burgess et al. | ............... | 606/252 |
| 7,241,074 B2 * | 7/2007 | Thomke et al. | ............... | 403/385 |
| 2002/0169448 A1 * | 11/2002 | Vanacker | ......................... | 606/61 |
| 2003/0114853 A1 * | 6/2003 | Burgess et al. | ................. | 606/61 |
| 2005/0228377 A1 * | 10/2005 | Chao et al. | ....................... | 606/61 |
| 2005/0228385 A1 * | 10/2005 | Iott et al. | ......................... | 606/61 |
| 2006/0271045 A1 * | 11/2006 | Hubbard et al. | ................ | 606/61 |

* cited by examiner

*Primary Examiner* — Eduardo C Robert
*Assistant Examiner* — Steven Cotroneo
(74) *Attorney, Agent, or Firm* — Carter, DeLuca, Farrell & Schmidt, LLP (57) ABSTRACT

Provided is a novel low profile transverse connector system having a first and second spinal rod connection member disposed at opposing ends of an elongated cross connection device, each connection member having a distal end configured to be capable of connecting to a spinal rod and a proximal end having a multidirectional articulation joint at which a centrally disposed cross connecting assembly is provided to attach the first and second connection members to each other, the first and second spinal rod connection members each defining two opposing compression slots that serve to facilitate a secure connection to spinal rods and to the cross connecting assembly by the tightening of only one locking screw. Also provided is a method of stabilizing vertebrae using the disclosed system.

17 Claims, 13 Drawing Sheets

FIG. 1

SECTION A-A
FIG.3

FIG.6A
SECTION B-B

FIG.6B
SECTION C-C

SECTION D-D
FIG. 9E

LOW PROFILE TRANSVERSE CONNECTOR

BACKGROUND OF THE INVENTION

1. Technical Field

The present invention relates to a novel transverse connector system for interconnecting a first and a second rod, which are in an approximately parallel relationship to each other. More particularly the present invention relates to a novel low profile transverse connector system having opposing ends, which are configured to be capable of being securely attached to a first rod or second rod with each end of the connector system being capable of independent multidirectional articulation. The present invention also relates to a multidirectional articulating transverse connector system, the length of which can be easily increased or decreased and locked or unlocked in the selected configuration as needed.

2. Background Art

Disease, the effects of aging, or physical trauma resulting in damage to the spine has been treated in many instances by fixation or stabilization of the effected vertebra. A wide variety of spinal fixation apparatuses have been employed in surgical procedures for correcting spinal injuries and the effects of spinal diseases. Many of these apparatuses commonly use a pair of longitudinal link rods running in a relative parallel relationship to each other and the spinal column. These rods are connected to coupling elements, which in turn are secured to the underlying vertebral bone by spinal bone fixation fasteners such as pedicle screws, hooks, and the like. The pair of longitudinal links can be held in position relative to one another by transverse connectors, also known as transverse bridge elements or cross-connectors.

As the technology of spinal surgery has developed and improved, each of the spinal fixation components has also undergone improvements and modifications to address the short-comings of conventional spinal appliances. The natural anatomical variations in the spinal column of a subject are such that implanted spinal rods while approximating a parallel relationship one to the other can vary from that parallel relationship considerably and in multiple planes. For this reason, any transverse connector used to attach the two rods to each other should not be of a rigid design without the ability to be re-configured as needed during the process of implanting and attaching to the two opposing rods. While some improvements have been made in the articulation and re-configuration operation of transverse connectors during the implantation and rod connection process, a continuing need exists to provide an improved multidirectional articulating transverse connector that can adapt to a wide variance in the contours of the spinal column. Further, a need exists to provide such a transverse connector that also has a low profile and a smooth contoured surface, thereby reducing the potentially negative impact of the implanted appliance on the overlying and surrounding soft tissue of the subject into which the appliance has been surgically implanted.

In addition to meeting the need of providing a multi-planar articulating transverse connector to securely connect the two opposing spinal rods together a requirement exists to provide a transverse connector that is capable of being easily adjusted to increase or decrease the length between the two opposing bone connection points to accommodate natural anatomical variances and once selected, to lock or unlock the device in the selected configuration.

Conventional efforts to meet this need have fallen short of the desired transverse connector configuration. For example, U.S. Pat. No. 6,554,832, issued to Shluzas, as best seen in FIGS. 2 and 4 of that patent, provides a transverse connector, which includes first and second connector members for connection to the respective first and second spinal rods. The two connector members are connected one to the other by a connecting rod, which can be withdrawn or extended in alignment with the longitudinal axis of the cross-connector for purpose of adjusting the length thereof. As shown in FIGS. 2 and 4 of the Shluzas patent, the articulation of the connecting members to align with the two opposing spinal rods is limited to a single, centrally disposed ball joint (50). Importantly, the pivoting movement of the Shluzas connector is limited to movement within the same horizontal plane relative to the longitudinal axis of the spinal column. Thus, while the device of Shluzas does permit some limited adjustment in length and azimuth of the device, it is configured to structurally prohibit any upward or downward movement in relation to the surface plane of the spinal column. That is, the elevation of one end of the Shluzas connector relative to the other end of the connector cannot be adjusted. Thus, while the Shulzas design does provide some flexibility in adapting the alignment of the transverse connector to the opposing spinal rods, it falls short of the greater degree of adaptability that could be obtained by a truly multi-planar transverse connector having multiple articulating points.

For reasons discussed above a continuing need exists for a transverse connector system that provides ease of operation by the surgeon to simultaneously adjust in multiple dimensions one spinal rod connecting end of the system in relation to the other spinal rod connecting end of the system and to provide a device having a very low profile and smooth contours for surfaces in contact with adjacent soft tissue.

SUMMARY OF THE DISCLOSURE

The transverse connector system and method of application of the present invention provides a novel transverse connector having a first and second spinal rod connection member at opposing ends of an elongated cross connector device, each connection member having a distal end configured to be capable of connecting to a spinal rod and a proximal end having a multidirectional articulation joint at which a centrally disposed cross connecting assembly is provided to attach the first and second connection members to each other, the first and second spinal rod connection members each defining two opposing compression slots that serve to facilitate a secure connection to spinal rods and to the cross connecting assembly by the tightening of only one locking screw.

Also provided is a novel transverse connector system having two opposing spinal rod connection members, each located at an opposing end of the system and connected one to the other by a centrally disposed low profile cross connecting assembly, the cross connecting assembly including a first cross member element and a second cross member element, which are slidably connected one to the other by a selectively lockable cross connecting assembly joint.

Also provided is a novel transverse connector system having two opposing spinal rod connection members and a low profile cross connecting assembly for connecting the first and second spinal rod connection members to each other, the cross connecting assembly including a first cross member element and a second cross member element, which are slidably connected one to the other by a selectively lockable cross connecting assembly joint.

Also provided is a novel transverse connector system having a first and second spinal rod connection member, each having a respective first or second articulation joint by which a cross connecting assembly can connect the first and second spinal rod connection members to each other to form the system, each of the spinal rod connection members defining at least one compression slot configured to facilitate compression of the connection member and locking of the first or second connection member to a respective first or second spinal rod while simultaneously locking the respective articulation joint into a selected configuration relative to the cross connecting member.

Also provided is a novel transverse connector system having a first and second spinal rod connection member, each having a respective first or second articulation joint by which a centrally disposed cross connecting assembly can connect the first and second spinal rod connection members to each other to form the system, the first and second spinal rod connection members each having at least one compression slot configured to facilitate locking of the first or second spinal rod connection member to a respective first or second spinal rod while simultaneously locking the respective articulation joint into a selected configuration relative to the cross connecting assembly.

Also provided is a method of stabilizing spinal vertebrae, the method including providing a novel transverse connector having a first and second spinal rod connection member at each respective end of the system, each connection member having a distal end configured to be capable of connecting to a spinal rod and a proximal end having a multidirectional articulation joint at which a centrally disposed cross connecting assembly is provided to attach the first and second connection members to each other and implanting the novel transverse connector into a subject in need thereof.

Also provided is a kit, which includes at least one a novel transverse connector having a first and second spinal rod connection member at each respective end of the system, each connection member having a distal end configured to be capable of connecting to a spinal rod and a proximal end having a multidirectional articulation joint at which a centrally disposed cross connecting assembly is provided to attach the first and second connection members to each other.

BRIEF DESCRIPTION OF THE DRAWINGS

The foregoing and other features of the novel transverse connector system will become apparent to one skilled in the art to which the disclosed system and devices relate upon consideration of the following description of exemplary embodiments with reference to the accompanying drawings, wherein.

DETAILED DESCRIPTION OF PREFERRED EMBODIMENTS

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

The low profile transverse connector system provides an elongated device, generally shown at 10 in FIGS. 1, 2A-B, 3, 4, 11A-C and 12, which includes a first and a second spinal rod connection member 12, 14, which are disposed at opposing first and second ends 16, 18 of the device 10, the two spinal rod connection members 12, 14 being connected one to the other by a cross member connecting assembly 20.

The two spinal rod connection members 12, 14 are each configured to be selectively and releasably secured to a spinal rod, which in turn can be secured to the underlying bone of a subject's spinal column as needed. As shown in FIGS. 1, 2B, 3, 4, 5B, 6A, 6C, 11B, 11C and 12, the spinal rod connection members 12, 14 are each configured at their most distal ends, that is at the first and second ends 16, 18 respectively of the device 10 to define a first and a second spinal rod connection passage 22, 24, the spinal rod connection passages 22, 24 being opened laterally toward the first or second end 16, 18 of the device 10. The outermost edges of the respective laterally opened spinal rod connection passages 22, 24 can be configured to provide an upper and a lower spinal rod retention lip 26, 28, each of which projects one toward the other so as to narrow the lateral opening of the spinal rod connection passages 22, 24 and to thus facilitate the spinal rod retention capability of the two spinal rod connection passages 22, 24.

The first and second spinal rod connection members 12, 14 are each sized and configured at their most proximal ends 30, 32 to define a ball joint receptacle 34, 36, each of the ball joint receptacles 34, 36 having a lateral opening sized and configured to receive a correspondingly sized ball joint in a snap-fit assembly manner.

As shown in FIGS. 1, 2A, 3, 4, 11A-C and 12, the upper surface 38 of each of the first and second spinal rod connection members 12, 14 defines a spinal rod locking screw receptacle 40, which is sized and configured to receive a spinal rod locking screw 42. The spinal rod locking screw receptacle 40, as best shown in FIGS. 6B-C is provided with threads only in the lower portion 44 of the receptacle 40; that is, that portion of the receptacle that is found below the elevation of the spinal rod connection passages 20, 22. The upper portion 46 of the spinal rod locking screw receptacle 40, located above the level of the spinal rod connection passages 20, 22 is unthreaded but is provided with a inwardly directed annular restricting ledge 48 that is sized and configured to define a passage that permits the threaded portion 50 of a locking screw 42 to pass freely pass through until the threaded portion 50 of the locking screw 42 engages the lower threaded portion 44 of the spinal rod locking screw receptacle 40. In operation, as the threaded portion 50 of the spinal rod locking screw 42 is threaded deeper into the threaded portion 44 of the spinal rod locking screw receptacle 40, the outwardly directed flange 52 on the underside of the spinal rod locking screw head 54 is brought into contact with the inwardly directed annular restricting ledge 48 in the upper portion 46 of the spinal rod locking screw 42. As the spinal rod locking screw 42 is manually screwed into the threaded portion 44 of the spinal rod locking screw receptacle 40, the flange 52 on the underside of the screw head 54 exerts compressive forces against the inwardly directed annular restricting ledge 48.

As shown in FIGS. 1, 2B, 4, 5B, 6B-C, 11B-C and 12, each of the spinal rod connection members 12, 14 is configured to define a first and a second compression slot 56, 58, which from opposing directions in the body of the spinal rod connection members 12, 14 can break the external integrity of the members 12, 14 through the defining wall of the spinal rod connecting passages 22, 24 and the ball joint receptacles 34, 36. Each of these compression slots 56, 58 being defined to pass one over the other through only a limited portion of the body of the connection members 12, 14. By thus configuring the pair of overlying compression slots 56, 58 to have opposing sides of origin and thus opposing directions of penetration into the body of the connection members 12, 14, a connection member is provided that can react to the above described compressive forces of an inwardly manipulated spinal rod locking screw 42 so as to bring those compressive forces to bear on both the spinal rod connection passages 22, 24 and the ball joint receptacles 34, 36.

Figure 9A:
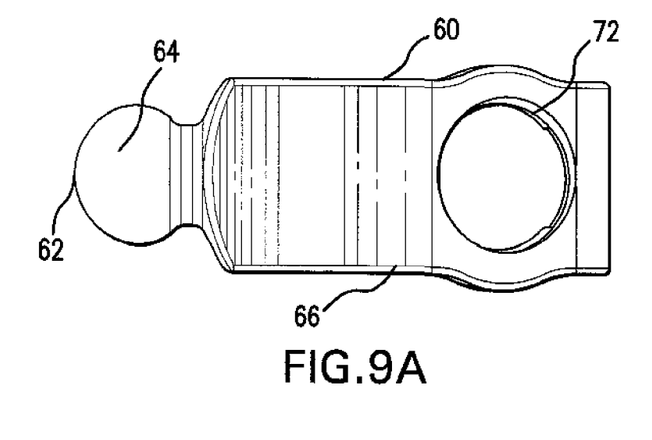
FIGS. 9A, 9B, 9C, 9D, and 9E respectively show a top, side, end, isometric, and cross sectional view D-D of a first cross member element of the cross member connecting assembly of the novel transverse connector.
Figure 9B:
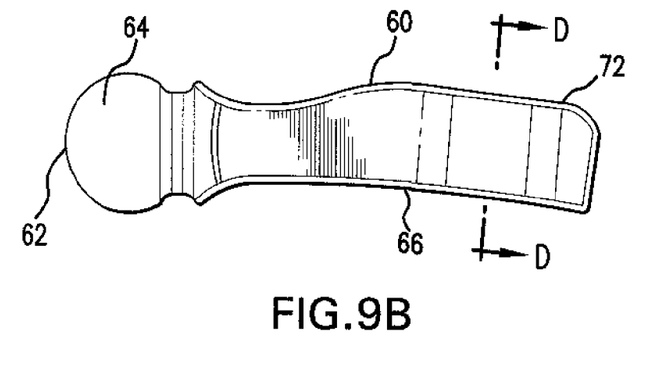
Figure 9C:
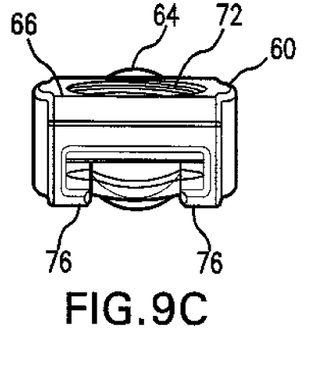
Figure 9D:
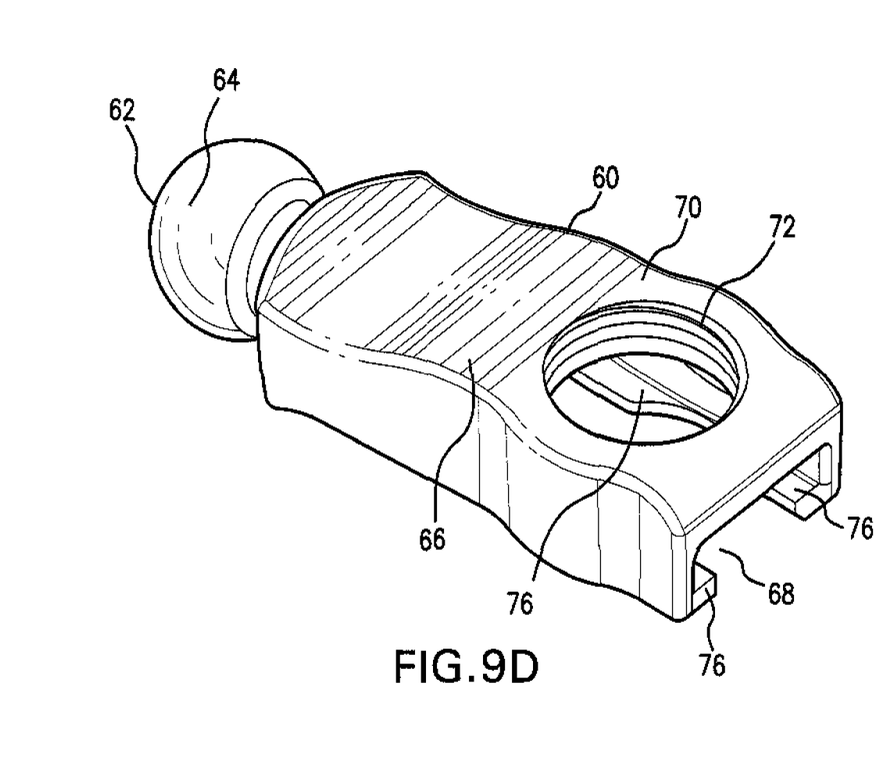
Figure 9E:
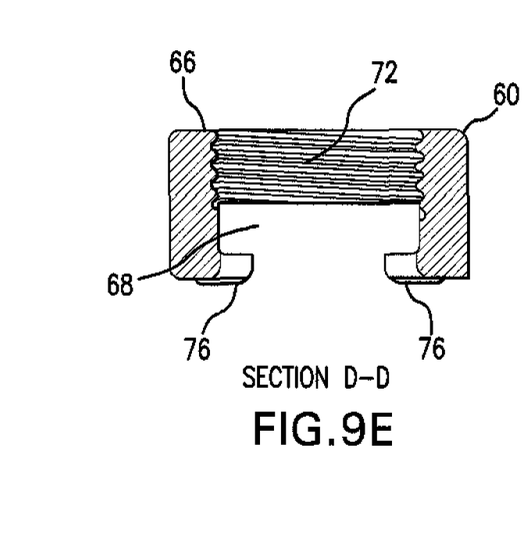

As shown in FIGS. 1, 2A-B, 3, 4, 9A-E and 10A-C the opposing spinal rod connection members 12, 14 are preferably connected one to the other by a cross member connecting assembly 20, which includes a first cross member element 60 that includes at a distal first end 62 a first articulating ball 64 that is sized and configured to fit into and articulate within the first ball joint receptacle 34 of the first spinal rod connection member 12. The first cross member element 60 of the cross member connecting assembly 20 also includes an elongated arm 66 configured as an external sleeve having an internally defined receiving passage 68. As shown in FIG. 9D the receiving passage 68 is preferably configured to be of a flattened nature having a partially open underside defined by opposing inwardly directed passage ridges 76; however, a receiving passage 68 which is of a rounded, ovoid, square or other shape and is completely enclosed would not depart from the inventors conception of the invention. The upper surface 70 of the first cross member can define a cross member connecting assembly locking screw receptacle 72, which can be sized and configured to receive a cross member connecting assembly locking screw 74, a non-limiting example of which is shown in FIGS. 1, 2A, 3, 4, 5 and 8A-C. Importantly, the upper extent of the assembly locking screw 74 when fully seated in the receptacle 72 is approximately flush with or below the level of the upper surface 70 of the first cross member element 60 so as to provide an extremely low profile for the device and thus reduce contact and trauma that might be imposed on overlying soft tissue of a subject.

As shown in FIGS. 1, 2A-B, 3, 4 and 10A-C, the cross member connecting assembly 20, also includes a second cross member element 78 having at a distal first end 80 a second articulating ball 82 that is sized and configured to fit into and articulate within the second ball joint receptacle 36 of the second spinal rod connection member 14. The second cross member element 78 of the cross member connecting assembly 20 also includes an elongated insertion arm 86, which is configured to correspond to the shape of the sleeve of the first cross member element 60. The preferred configuration of a generally flattened shape for the elongated insertion arm and its receiving sleeve 66 serves to promote a lower profile for the device 10, however, as earlier indicated any shape for the complementary portions of the first and second elements, the elongated arm sleeve 66 and the insertion arm 86 are within the concept of the invention. The underside of the insertion arm 86 can be provided with an insertion arm guide 88 which is disposed along the longitudinal axis of the arm 86. As the insertion arm 86 of the second cross member element 78 slidably passes into the complimentary shaped receiving passage 68 of the first cross member element 60, the insertion arm guide 88 likewise passes between the opposing inwardly directed passage ridges 76 disposed along the underside of the first cross member element 60 of the cross member connection assembly 20. By this sliding operation of the insertion arm 86 inward or outward within the elongated arm sleeve 66 the length of the cross member connector assembly 20 and therefore the length of the device 10 can be selectively lengthened or shortened. In operation, when the desired length of the cross connecting assembly 20 is set, the assembly locking screw 74 can be manually inserted into the screw receptacle 72 located in the top of the elongated arm sleeve 66 so as to contact the insertion arm 86 slidably disposed within. As pressure from the screw 74 is increased the underlying insertion arm 86 can be securely locked in its respective position within the elongated arm sleeve 66. Retraction of the screw 74 and release of the downward force on the insertion arm 86 can release the elongated arm 86 from its locked position and again allow sliding motion to reset the length of the cross member connecting assembly 20 as desired.

Figure 1:
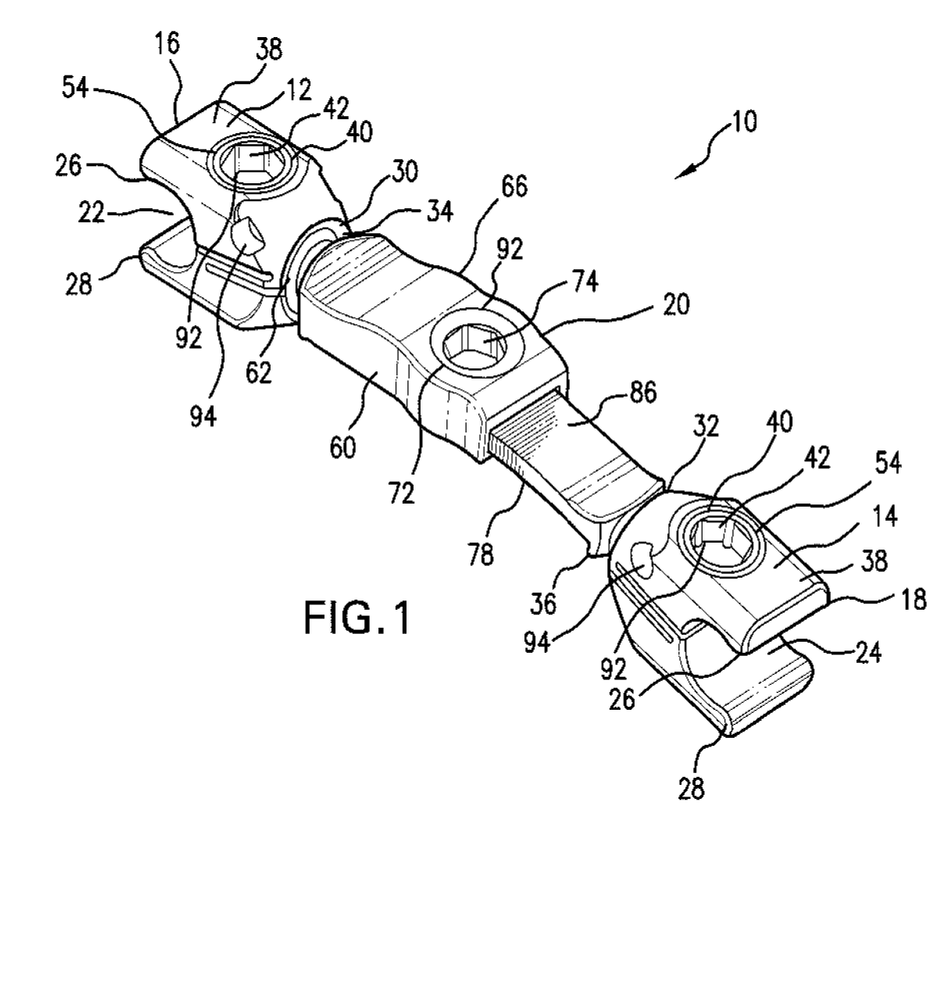
FIG. 1 shows an isometric view of the novel transverse connector system.
Figure 2A:
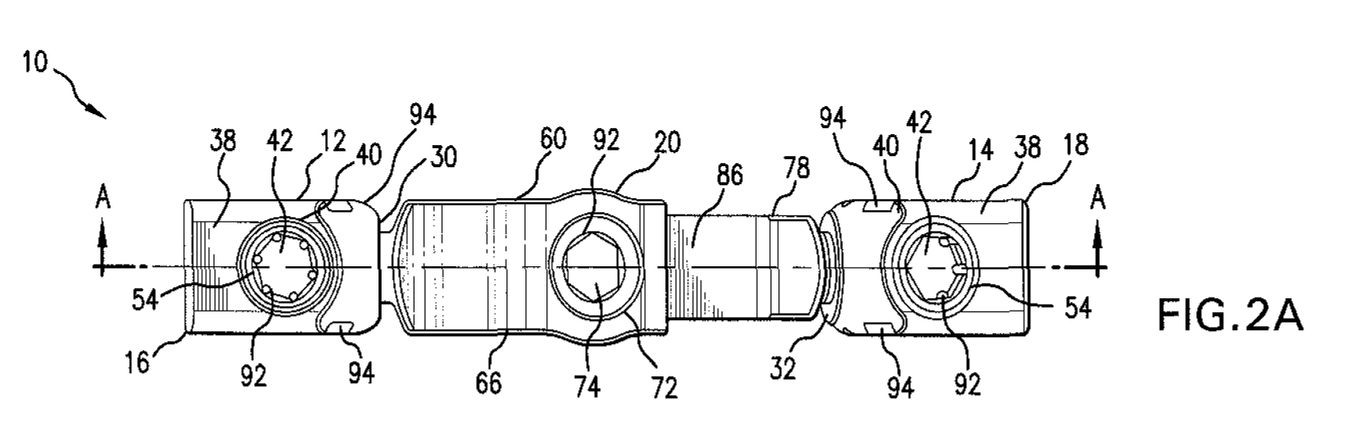
FIGS. 2A and 2B respectively show top and side views of the novel transverse connector system.
Figure 2B:
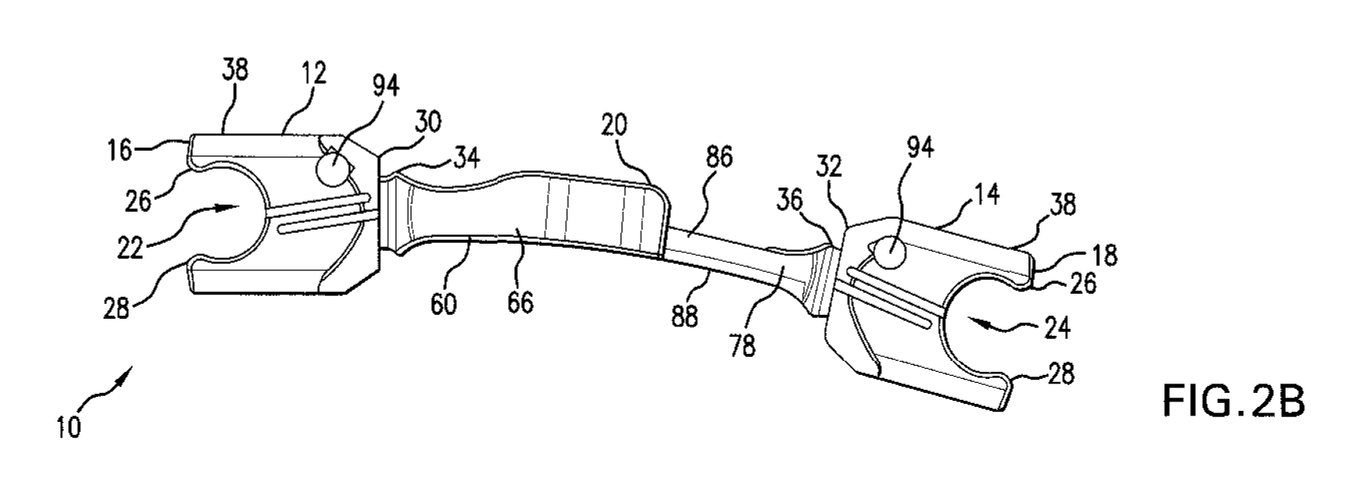
Figure 3:
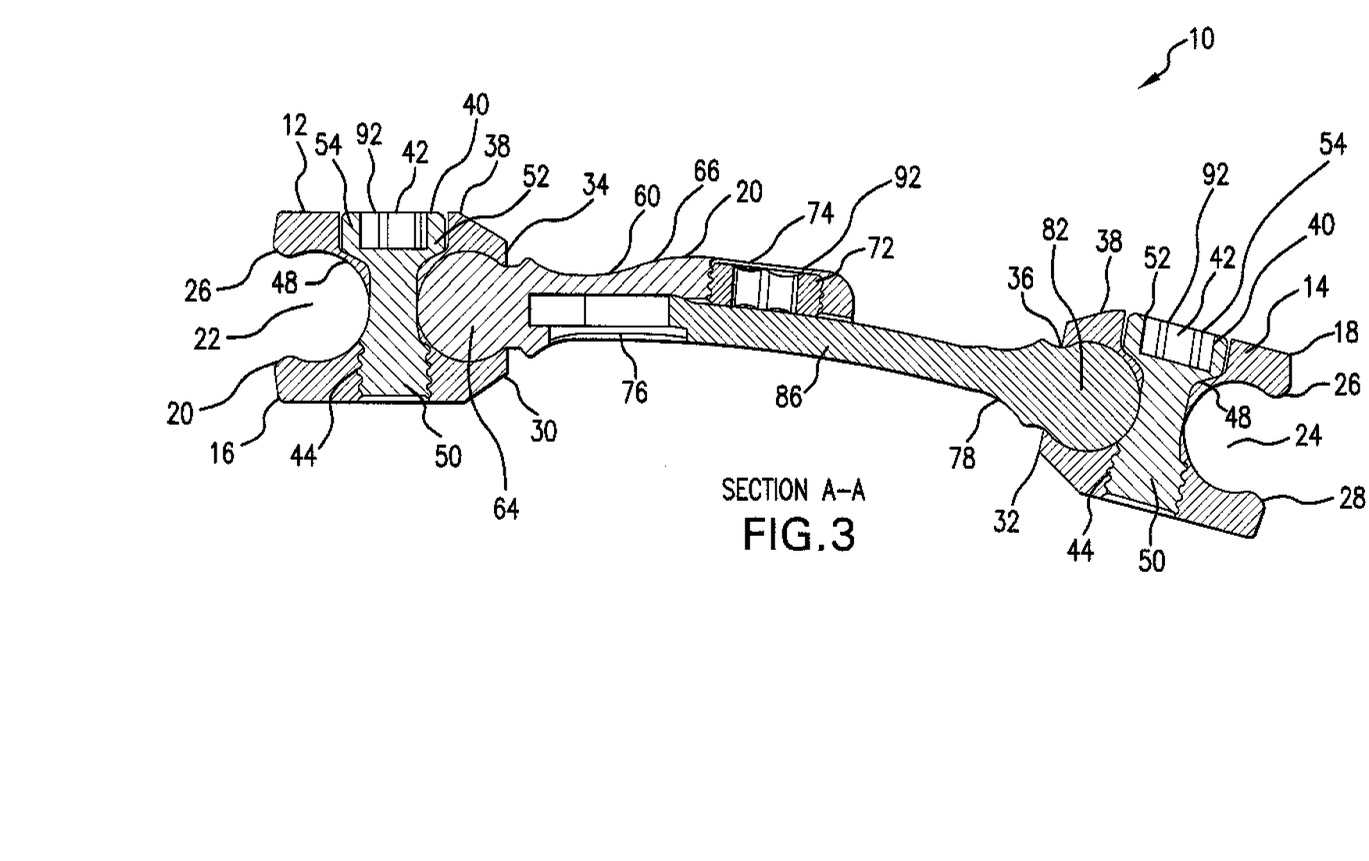
FIG. 3 shows cross-sectional view A-A of the novel transverse connector system shown in FIG. 2.
Figure 4:
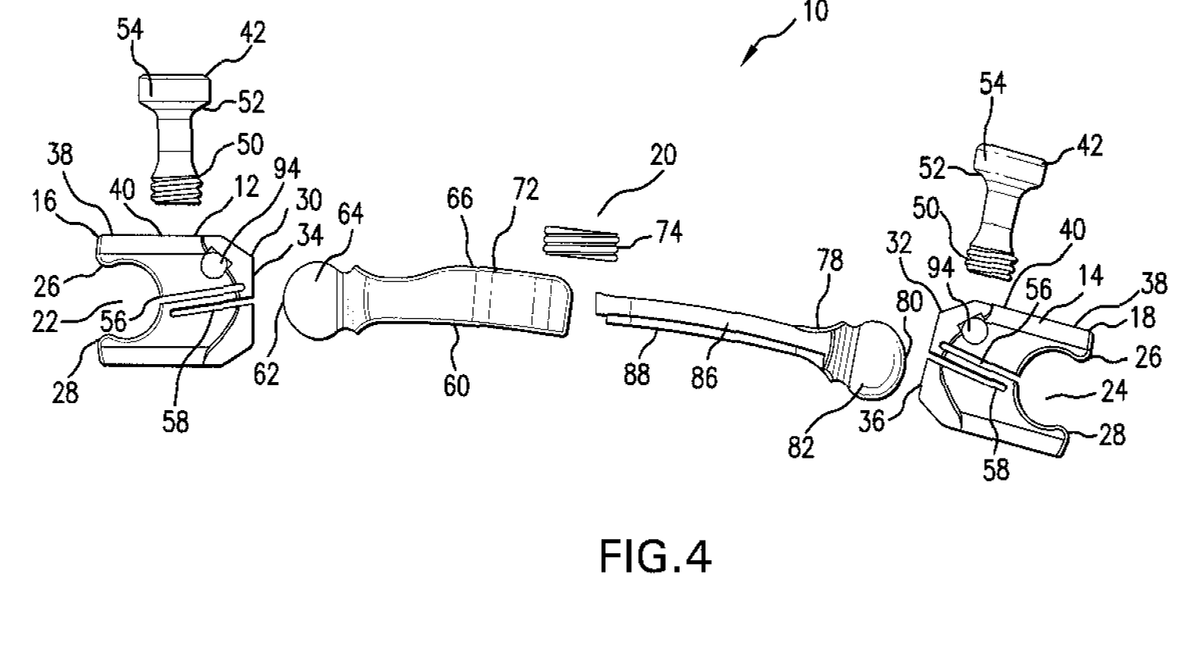
FIG. 4 shows an exploded view of the novel transverse connector system.
Figure 5A:
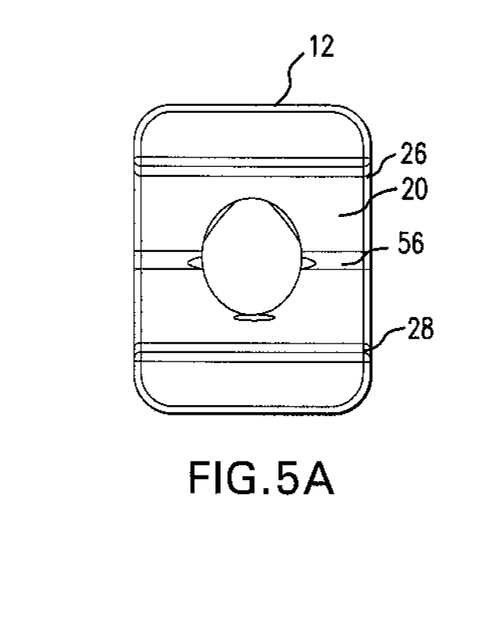
FIGS. 5A and 5B respectively show end and side views of a spinal rod connection member of the novel transverse connector system.
Figure 5B:
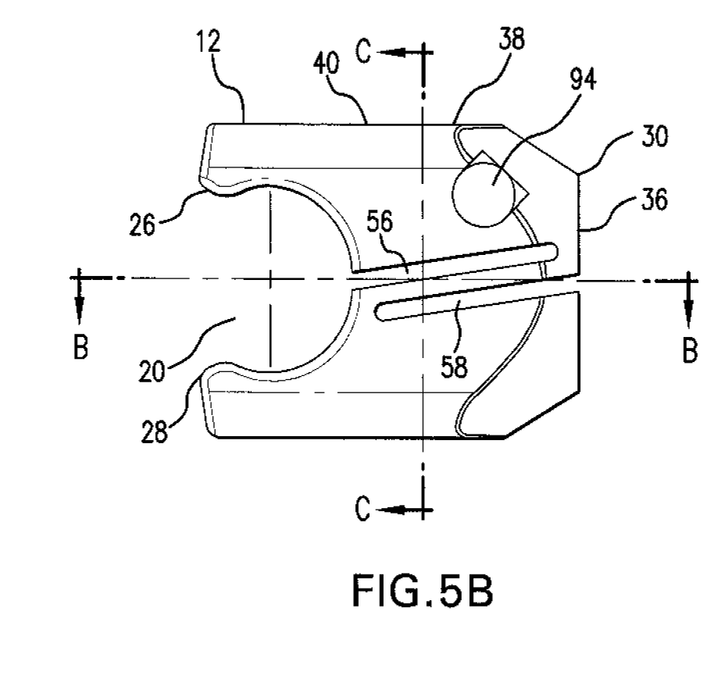
Figure 6A:
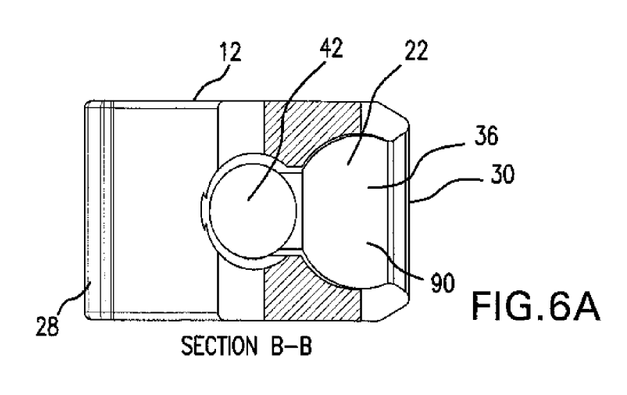
FIGS. 6A, 6B and 6C respectively shows cross-sectional view B-B in FIG. 6A, cross sectional view C-C in FIG. 6B, and an isometric view in FIG. 6C of the spinal rod connection member of the novel transverse connector system shown in FIG. 5-B.
Figure 6B:
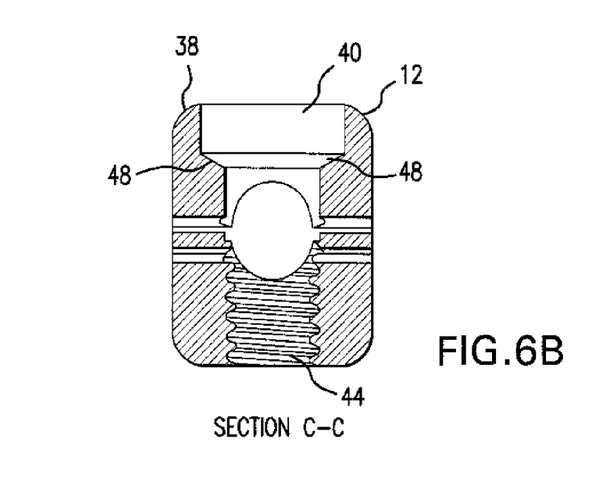
Figure 6C:
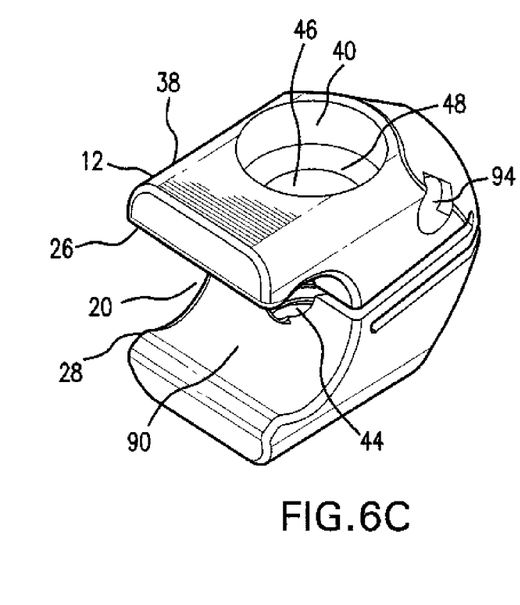
Figure 7A:
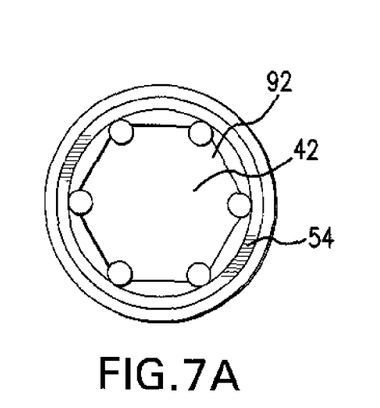
FIGS. 7A, 7B and 7C respectively show a top, side, and isometric view of a spinal rod connection member locking screw of the novel transverse connector system.
Figure 7B:
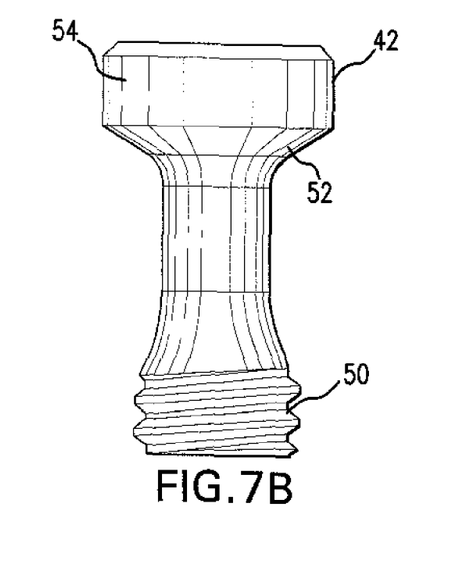
Figure 7C:
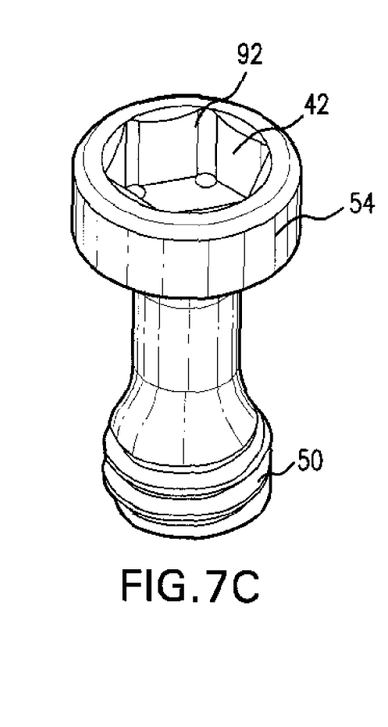
Figure 8A:
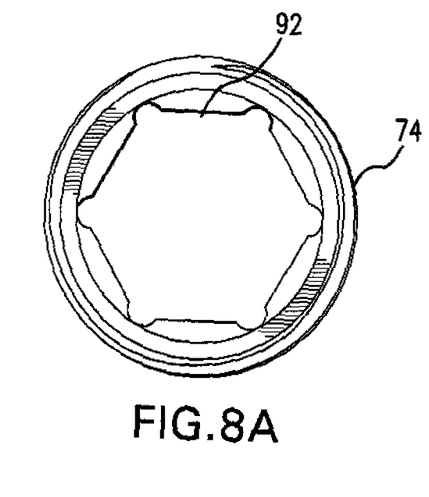
FIGS. 8A, 8B and 8C respectively show a top, side, and isometric view of a connecting member locking screw of the novel transverse connector system.
Figure 8B:
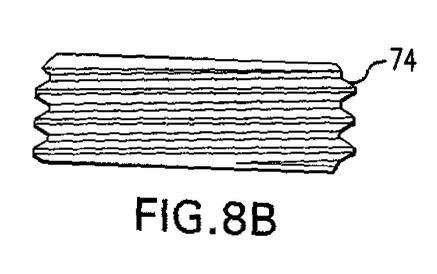
Figure 8C:
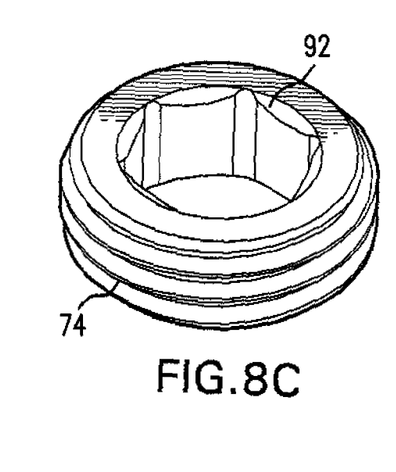
Figures 10A, 10B, 10C:
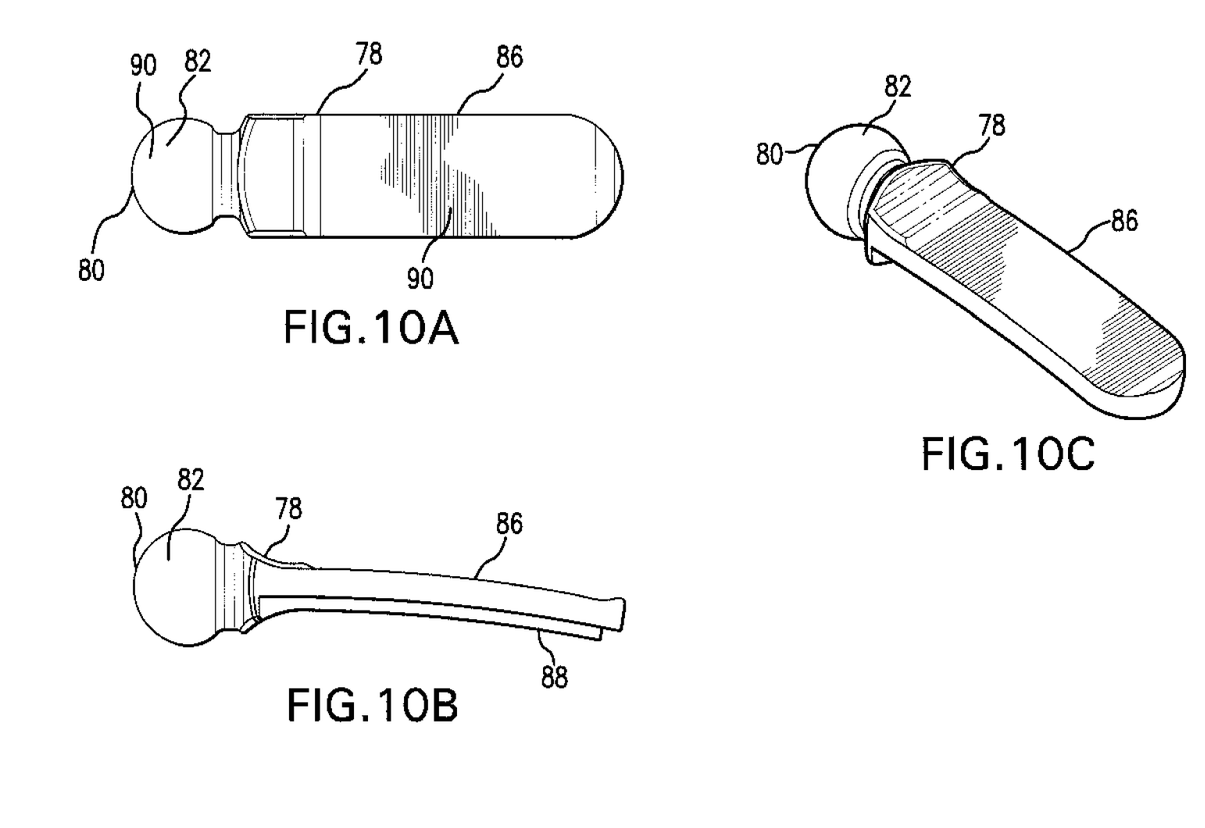
FIGS. 10A, 10B and 10C respectively show a top, side and isometric view of a second cross member element of the cross member connecting assembly of the novel transverse connector.
Figures 11A, 11B, 11C:
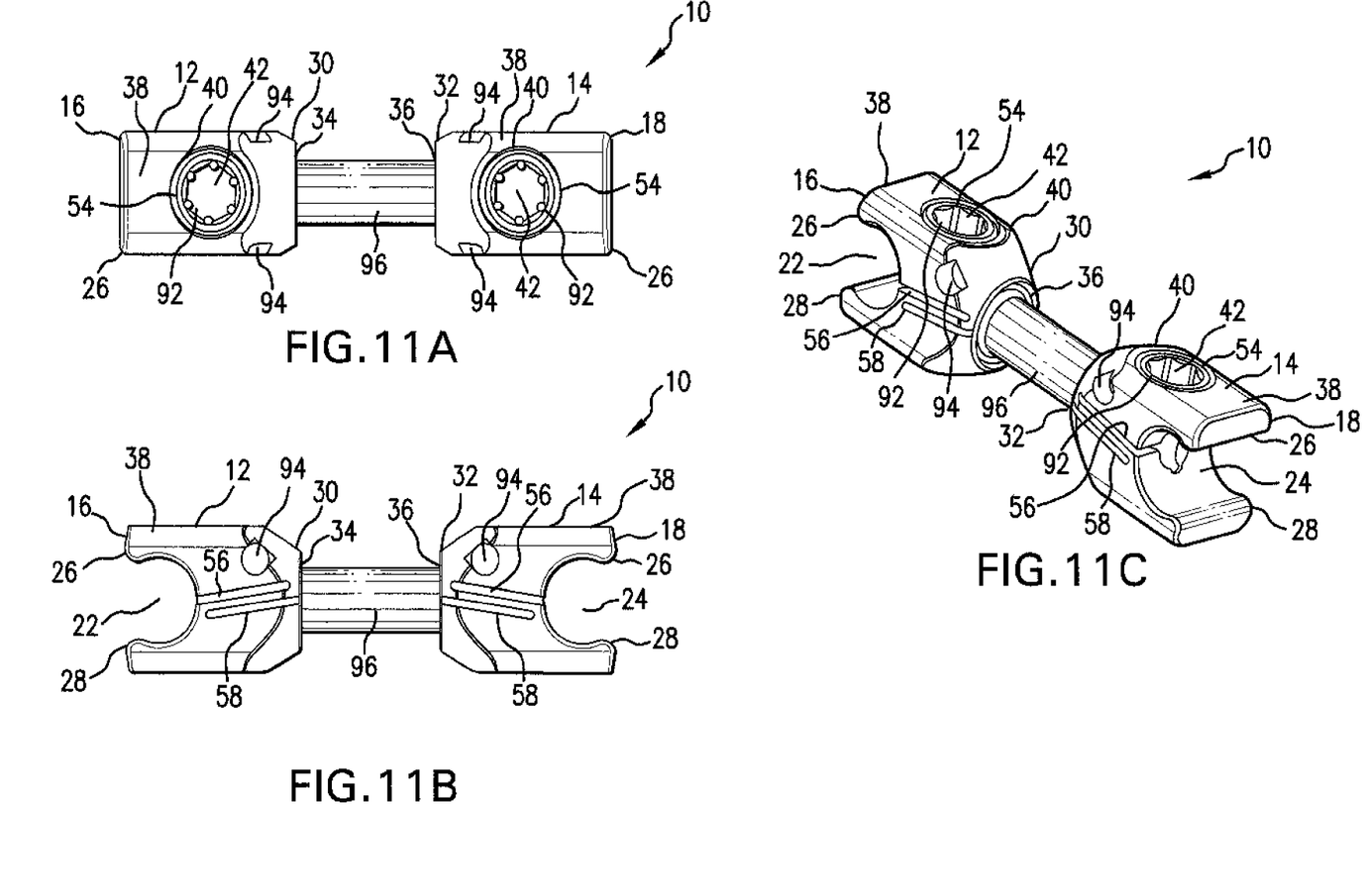
FIGS. 11A, 11B and 11C respectively show a top, side and isometric view of a novel transverse connector having a set length.

As shown in the non-limiting examples of FIGS. 6A, 6C and 10A, any articulating surface of the device can be treated, machined, scored, or in any known manner textured to provide a roughened or textured surface 90 that can serve to increase the locking contact of those surfaces when the articulating members are set in place and the associated locking screws are manipulated to lock the device in the desired configuration.

As shown in FIGS. 1, 2A, 7A-C, 8A-C and 11A-C, each of the spinal rod locking screws 42 and the cross member connecting assembly locking screw 74 is provided with tightening/loosening tool gripping elements 92 located with a recess in the head of the respective screw. The configuration of these screw head recessed gripping elements 92 are of complimentary configuration to the tool provided for tightening or loosening the particular locking screw and can be of any configuration without departing from the concept of the invention.

As shown in FIGS. 1, 2A-B, 4, 5B, 6C, 11A-C and 12, each of the first and second spinal rod connection members 12, 14 can be provided with at least one and preferably two opposing grasping recesses 94, which are sized and configured to receive a grasping instrument used by the operator to securely and releasably grasp each of the spinal rod connection members 12, 14 for purposes of manipulating the members 12, 14 into a proper engaging relationship with a respective spinal rod. The grasping recesses 94 can be of any configuration suitable for receiving the grasping instrument used by the operator. These grasping recesses can also be configured as protrusions or any other configuration as desired so long as they facilitate the grasping and manipulation of the member by the user during the insertion process of the device 10.

In operation, a user as indicated above can manipulate the device 10 into position relative to two opposing and relatively parallel spinal rods, independently connecting the first and second spinal rod connection members 12, 14 to their respective spinal rods and adjusting the alignment of the member 12, 14 with the centrally connected cross member connecting assembly 20 by manipulating the respective first ball 64 within the first ball joint receptacle 34 and the second ball 82 with the second ball joint receptacle 36 and adjusting the length of the cross member connector by sliding the insertion arm 82 to a desired position within the elongated arm sleeve 66. When all members and of the device 10 are properly positioned, the user can by tightening the provided locking screws 42 and 74, lock the device into a selected configuration relative to the two opposing spinal rods. Adjustment or removal of the device can be easily achieved by loosening the locking screws 42 and 74.

Figure 12:
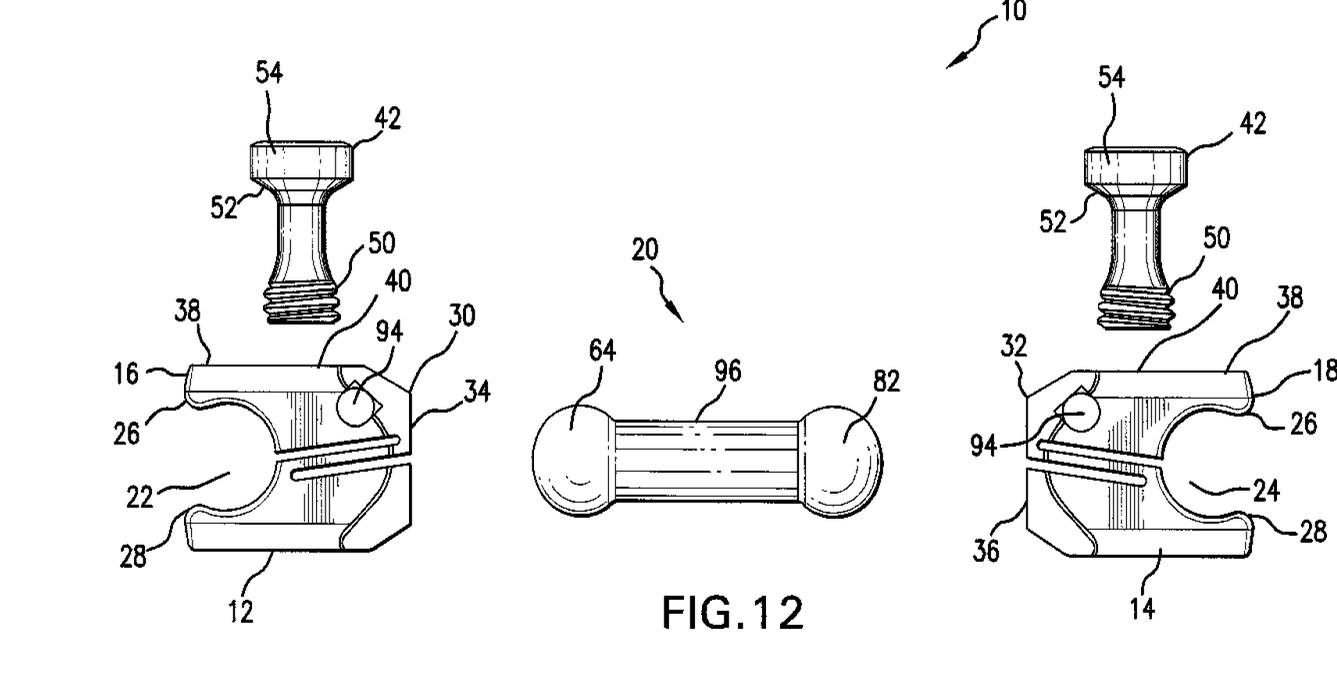
FIG. 12 shows an exploded view of the novel transverse connector having a set length shown in FIGS. 11A-C.

FIG. 12 shows the device 10 in a set length configuration, wherein the first spinal rod connection member 12 and the second spinal rod connection member 14 are connected one to the other by an elongated cross connecting member 96 terminating at each end with a first articulating ball 64 and a second articulating ball 82, which rotatably connect to and articulate with the first connection member 12 and the second connection member 14 in the same manner as described above. This embodiment of the device 10 simplifies the insertion and adjustment of the device and is indicated for use when adjustment of the length of the device is not required.

The above described method of use of the novel low profile transverse connector system 10 can be employed with the use of spinal rods and associated bone connection devices as a method of stabilizing or fixing injured or diseased vertebrae and if necessary, multiple devices 10 can be employed along the length of the opposing spinal rods.

The device 10 can be manufactured as components by methods known in the art, to include, for example, molding, casting, forming or extruding, and machining processes. The components can be manufactured using materials having sufficient strength, resiliency and biocompatibility as is well known in the art for such devices. By way of example only, suitable materials can include implant grade metallic materials, such as titanium, cobalt chromium alloys, stainless steel, or other suitable materials for this purpose. It is also conceivable that some components of the device can be made from plastics, composite materials, and the like.

It is also within the concept of the inventors to provide a kit, which includes at least one of the novel transverse connectors. The kit can also include additional orthopedic devices and instruments; such as for example, instruments for tightening or loosening the locking screws, spinal rods, hooks or links and any additional instruments or tools associated therewith. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A low profile transverse connector system, comprising:
a first and a second spinal rod connection member, each spinal rod connection member having a spinal rod connection passage at a first end and a ball joint receptacle at the opposing second end, said first and second spinal rod connection members each including an integral body having a first and a second opposing compression slot, each spinal rod connection member defining a locking screw receptacle sized and configured to receive a locking screw capable of exerting compressive forces on said respective spinal rod connection passages and said respective ball joint receptacles by compressing said respective first and second compression slots;
said first and second spinal rod connection members being connected one to the other by an elongated cross connecting member, said cross connecting member terminating at each end with an articulating ball that is sized and configured to articulate within said respective ball joint receptacles of said first and second spinal rod connection members.

2. The transverse connector system of claim 1, wherein said cross connecting member is a cross member connecting assembly, said assembly comprising:
a first elongated arm defining a sleeve and a locking screw receptacle,
a second insertion arm sized and configured to slidably pass within said elongated arm sleeve, and
a cross member connecting assembly locking screw having an underside defining an outwardly directed flange, said screw being capable of exerting compressive forces against said insertion arm positioned with said elongated arm sleeve.

3. The transverse connector system of claim 2, wherein said first compression slot originates in and interrupts the external surface of the spinal rod connection passage and said second compression slot originates in and interrupts the external surface of the ball joint receptacle.

4. The transverse connector system of claim 2, wherein said locking screw receptacle of each of said spinal rod connection members includes an upper portion, said upper portion having no threads and including an inwardly directed annular restricting ledge, said ledge sized and configured to define a opening which allows unrestricted downward movement of a threaded portion of said locking screw but restricting downward motion of the outwardly direct flange at the underside of the locking screw head.

5. The transverse connector system of claim 4, wherein said spinal rod connection members each includes a lower portion, said lower portion defining the threaded portion of the said locking screw receptacle, said threaded portion be configured to engage threads of an inserted locking screw.

6. The transverse connector system of claim 2, wherein said elongated arm sleeve and said inwardly and slidably disposed insertion arm are of a flattened configuration so as to present a low profile.

7. The transverse connector system of claim 6, wherein said elongated arm sleeve is provided with an open along the length of the sleeve bottom, said open portion being defined on each side by opposing inwardly directed passage ridges and said insertion arm includes a downwardly directed insertion arm guide, said insertion arm guide being sized and configured to slidably pass between said opposing inwardly directed passage ridges.

8. The transverse connector system of claim 2, wherein at least one of the articulating surfaces of said ball and ball receptacle and said internally slidably disposed insertion arm and elongated arm sleeve are provided with a textured surface.

9. The transverse connector system of claim 2, wherein said locking screws when fully seated do not extend above the surface level of the device.

10. A method of stabilizing a vertebral body, the method comprising, providing at least one transverse connector system according to claim 1,
    providing at least two spinal rods,
    surgically accessing the spinal column of a subject in needed of vertebral stabilization,
    positioning said two spinal rods along the spinal column of the subject as desired and connecting the two spinal rods, one to other, using said transverse connector.

11. A kit comprising at least one system according to claim 1 and at least one other tool or instrument for use in orthopedic surgery.

12. The transverse connector system of claim 1, wherein manipulation of the locking screw exerts compressive forces on both the spinal rod connection passage and the ball joint receptacle such that a spinal rod is locked within the spinal rod connection passage and the articulating ball of the elongated cross connecting member is locked within the ball joint receptacle.

13. The transverse connector system of claim 1, wherein each of the compression slots are defined to pass one over the other through a portion of the spinal rod connection members and each of the compression slots are configured to have opposing sides of origin and opposing directions of penetration into the spinal rod connection members to facilitate exerting compressive forces on both the spinal rod connection passage and the ball joint receptacle via the locking screw.

14. A transverse connector system comprising:
    first and second connection members, each connection member having a passage at a first end and a receptacle at an opposing second end, each of said first and second connection members having an integral body including first and second opposing compression slots, each of said first and second connection members including a screw opening;
    first and second screws insertable into respective screw openings;
    a connecting assembly for coupling the first and second connection members, the connecting assembly including:
        a first arm having a sleeve, a screw receptacle, and a first ball disposed at one end thereof, the first ball rotatably disposed in the receptacle of the first connection member;
        a second arm configured to slidably pass within said arm sleeve, the second arm including a second ball disposed at one end thereof, the second ball rotatably disposed in the receptacle of the second connection member; and
        a locking screw, said screw being capable of exerting compressive forces against said insertion arm positioned with said elongated arm sleeve, wherein said elongated arm sleeve is provided with an open portion along the length of the sleeve bottom, said open portion being defined on each side by opposing inwardly directed passage ridges and said insertion arm includes a downwardly directed insertion arm guide, said insertion arm guide being configured to slidably pass between said opposing inwardly directed passage ridges.

15. The transverse connector of claim 14, wherein rotation of one of the first and second screws in the screw opening compresses the first and second compression slots thereby compressing said passage and said receptacle.

16. The transverse connector system of claim 14, wherein manipulation of the first and second screws of each of the first and second connection members exerts compressive forces on both the passage and the receptacle, respectively, such that a spinal rod is locked within the passage and the ball of the elongated cross connecting member is locked within the receptacle.

17. The transverse connector system of claim 14, wherein each of the compression slots are defined to pass one over the other through a portion of the spinal rod connection members and each of the compression slots are configured to have opposing sides of origin and opposing directions of penetration into the spinal rod connection members to facilitate exerting compressive forces on both the passage and the receptacle via the screw.

\* \* \* \* \*